(12) United States Patent
LaBorde

(10) Patent No.: US 6,607,922 B2
(45) Date of Patent: *Aug. 19, 2003

(54) IMMUNOCHROMATOGRAPHIC ASSAY METHOD AND APPARATUS

(75) Inventor: Ronald T. LaBorde, San Diego, CA (US)

(73) Assignee: Quantum Design, Inc., San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/527,801

(22) Filed: Mar. 17, 2000

(65) Prior Publication Data

US 2003/0040124 A1 Feb. 27, 2003

(51) Int. Cl.$^7$ ............................................. G01N 33/543
(52) U.S. Cl. .................. 436/514; 436/518; 436/524; 436/530; 436/541; 436/807; 435/7.1; 435/7.93; 435/7.94; 435/287.7; 435/287.9; 435/288.7; 435/970; 422/56; 422/58; 422/59; 422/60; 422/99; 422/104
(58) Field of Search ................ 436/518, 524, 436/530, 541, 807; 435/7.1, 7.93, 7.94, 287.7, 287.9, 288.7, 970; 422/56, 99, 58, 104, 59, 60

(56) References Cited

U.S. PATENT DOCUMENTS

| | | | |
|---|---|---|---|
| 3,884,641 A | * | 5/1975 | Kraffczyk et al. |
| 3,981,776 A | | 9/1976 | Saxholm .............. 195/103.5 R |
| 4,554,088 A | * | 11/1985 | Whitehead et al. |
| 4,632,901 A | | 12/1986 | Valkirs et al. .................. 435/5 |
| 4,956,302 A | | 9/1990 | Gordon et al. .............. 436/161 |
| 5,075,078 A | | 12/1991 | Osikowicz et al. ........... 422/56 |
| 5,120,643 A | | 6/1992 | Ching et al. ................ 435/7.92 |
| 5,395,498 A | | 3/1995 | Gombinsky et al. ..... 204/182.8 |
| 5,445,970 A | | 8/1995 | Rohr ........................... 436/526 |
| 5,445,971 A | | 8/1995 | Rohr ........................... 436/526 |
| 5,476,796 A | | 12/1995 | Takahashi et al. ........... 436/526 |
| 5,578,577 A | | 11/1996 | Ching et al. ................... 514/21 |
| 5,591,645 A | | 1/1997 | Rosenstein ................... 436/514 |
| 5,602,040 A | | 2/1997 | May et al. ................... 436/514 |
| 5,622,871 A | | 4/1997 | May et al. ................... 436/514 |
| 5,645,798 A | * | 7/1997 | Schreiber et al. |
| 5,656,502 A | * | 8/1997 | MacKay et al. |
| 5,714,389 A | | 2/1998 | Charlton et al. ............. 436/514 |
| 5,798,273 A | | 8/1998 | Shuler et al. ................ 436/514 |
| 5,817,526 A | | 10/1998 | Kinoshita et al. ........... 436/526 |
| 5,869,345 A | | 2/1999 | Chandler |
| 5,879,951 A | | 3/1999 | Sy .............................. 436/514 |
| 5,900,379 A | * | 5/1999 | Noda et al. |
| 5,922,284 A | | 7/1999 | Kinoshita et al. ........... 422/68.1 |
| 5,925,573 A | | 7/1999 | Colin et al. .................. 436/525 |
| 5,939,252 A | | 8/1999 | Lennon et al. .................. 435/4 |
| 5,958,790 A | | 9/1999 | Cerny ......................... 436/501 |
| 5,968,839 A | | 10/1999 | Blatt et al. |
| 5,981,297 A | | 11/1999 | Baselt ......................... 436/514 |
| 5,998,220 A | | 12/1999 | Chandler ..................... 436/514 |
| 6,017,767 A | | 1/2000 | Chandler ..................... 436/514 |

FOREIGN PATENT DOCUMENTS

| | | | |
|---|---|---|---|
| GB | 2204398 A | * | 11/1988 |
| WO | WO 97/34150 | | 9/1997 |
| WO | WO 97/35205 | | 9/1997 |

* cited by examiner

*Primary Examiner*—Bao-Thuy L. Nguyen
(74) *Attorney, Agent, or Firm*—The Maxham Firm

(57) ABSTRACT

An immunochromatographic assay employing superparamagnetic particles to lable the target analytes. An opaque cover prevents misinterpretive readings in field situations and provides a protective surface on the porous membrane. Additional features include separability of the test strip from any backing or housing which is configured to support the strip, and that quantitative measurements of the target analytes are easily and accurately made by means of an electromagnetic reader device.

6 Claims, 3 Drawing Sheets

US 6,607,922 B2

IMMUNOCHROMATOGRAPHIC ASSAY METHOD AND APPARATUS

BACKGROUND OF THE INVENTION

1. Field of the Invention

This invention relates generally to immunoassays, and more specifically to an improved chromatographic assay, often referred to as a lateral flow assay, having a test strip employing susperparamagnetic particles as the labels for the analytes to be detected, where, as an additional feature, the analytical strip is removable for reading the quantity of analytes captured therein and for archival purposes.

2. Discussion of Related Art

Various chromatographic immunoassay techniques have been available for many years. One common aspect of known devices, particularly in the lateral flow technology, is that the assay is read visually, that is, by means of one or more optically readable lines on a test strip, typically held in a carrier, which may have various configurations. One end of the test strip is exposed to the sample, normally a body fluid of some type, being tested for the particular target analytes of interest. It is known that particular analytes are indicative of particular biological, environmental, and biohazard conditions, among others. For example, urine may be tested for pregnancy or ovulation and if the target analytes are present, the test is positive. Body fluids may be tested for the presence of other analytes indicative of biological conditions or they may be indicative of the presence of substances, such as drugs. Another example would be for testing water for contaminates. Examples of lateral flow assay methods and apparatuses, where the reading is normally conducted optically, are shown in U.S. Pat. Nos. 5,591,645; 5,798,273; 5,622,871; 5,602,040; 5,714,389; 5,879,951; 4,632,901; and 5,958,790.

A different technology is employed in other types of biological technologies employing magnetic particles or microbeads, sometimes more specifically termed superparamagnetic iron oxide impregnated polymer beads. These beads are employed to bind with the target analytes in the sample being tested and are then typically isolated or separated out magnetically. Once isolation has occurred, other testing may be conducted, including observing particular images, whether directly optically or by means of a camera. Examples of these technologies are disclosed in U.S. Pat. Nos. 3,981,776; 5,395,498; 5,476,796; 5,817,526; and 5,922,284. Another apparatus for detecting target molecules in a liquid phase is shown in U.S. Pat. No. 5,981,297 where magnetizable particles are employed and the output of magnetic field sensors indicates the presence and concentration of target molecules in the sample being tested. Other examples to sense magnetically using physical forces are disclosed in U.S. Pat. Nos. 5,445,970; 5,981,297 and 5,925,573.

There are several limitations or disadvantages to the known optically detected assays. Because they are optical, only surface changes (coloration, typically) can be detected. The target analytes may be in the sample solution but of such a low concentration that only a relatively few are captured in the capture zone in the porous membrane of the assay. This provides a faint or even non-optically detectable line, and a resultant false negative reading. Quantitative assessments are really only an estimation based on color intensity of the detection line. Because the prior art assays are optically read, they are subject to contamination by exposure, and light-caused degradation. Optical assays have a limited archival shelf life.

None of the known prior art employs magnetic particles in conjunction with lateral flow assay technology.

SUMMARY OF THE INVENTION

Broadly speaking, the invention relates to lateral flow immunoassay technology employing superparamagnetic particles as the labels for the analytes to be detected. The bound complexes of labeled particles and analytes are captured in predetermined areas or regions on the test strip and the presence and quantity of labeled analytes are then readable by magnetic means. An advantageous additional feature of the invention is that the test strip can be removable from the support member for archival purposes or for reading by an appropriate magnetic sensing device, or both.

A relatively standard lateral flow assay structure is employed but the invention greatly improves the sensitivity of the device over known lateral flow techniques. It provides a very rapid (a few seconds) measurement of the analytical region in the test strip. There are many advantages of using magnetic particles over known colored particles or other optical indicators in the prior art. These include linearity because magnetic detection is linear with respect to the amount of magnetic material present over a wide range, through at least four orders of magnitude. Time stability is also significant because magnetic particles are stable. The developed assay is available to be archived and retested as necessary. Further, magnetic particles are generally inert to biological systems and the environment so they not only remain stable, they are environmentally and biologically safe. Further, magnetic particles are already in widespread use throughout the diagnostics industry with other technologies so they are readily available. Other benefits of magnetic detection are that since the particles are superparamagnetic, they are magnetic only when in a magnetic field. This allows them to be freely manipulated in solution without aggregating.

Another significant advantage over the prior art optical lateral flow devices is that with this invention the total amount of analytes in the capture region of the test strip is measured as a single mass in one volumetric measurement by magnetic means. The permeability of magnetic fields is such that any analyte contained within the active region of the detector will be measured. This contrasts with optical sensing techniques in which only reporter-analyte interactions on or very near the surface are detectable. In this invention the strength of the magnetic signal increases directly with the mass of iron involved. This inherent linearity of magnetic detection contributes to sensitivity, accuracy and dynamic range. Finally, superparamagnetic particles are physically similar to collodial gold with regard to size, and may be easily adapted to a wide range of lateral flow assays. It is noted that collodial gold, as well as fluorescent latex particles, are typically employed in the prior art optically sensed immunological assay techniques.

In lateral flow technology, at one end of the porous membrane (the active part of the test strip) is the sample introduction area conventionally comprising a sample pad and a conjugate pad. In the prior art, the conjugate pad was the source of freely moveable colored particles, typically gold sols from collodial gold, or fluorescent latex particles. In the present invention, the moveable particles are the superparamagnetic particles which label the target analytes from the sample being introduced through the sample pad. The sample, together with the bound magnetic particle labels and target analytes, move with capillary action along the porous membrane and are captured in a predefined location called a capture region or capture zone. There may be more than one capture zone to enable multiplexing, that is, testing for more than one type of analyte at the same time in the same test strip. Excess analytes and the carrying liquid continue to move on through the capture zone to the other end of the porous membrane, sometimes forming a control line or zone separate from the capture zone. An added feature is that typically a wicking pad is mounted on the far end of the porous membrane to enhance the capillary action which drives the flow from the introduction at one end of the porous membrane through the entire length of the membrane.

The porous membrane typically is mounted on a relatively rigid support or base member, but in an advantageous embodiment a separation sheet, or adhesive layer, exists between the base member and the porous membrane. This enables very easy removal of the test strip, which normally would include the separation sheet, so that the test strip is a very thin element which may be magnetically sensed in an appropriate device. Since optical means are not employed and color at the capture zone has no meaning, the top of the porous member is preferably covered by another protective sheet or membrane which is not transparent. It may be completely opaque. This top sheet may also include pre-printed standards, which are employed for calibrating purposes so that the magnetic detector can be calibrated for each test to ensure complete accuracy. The protective sheet may not be a separate element in some cases, but may only be the upper surface of the membrane properly treated to function as a protective sheet or surface.

BRIEF DESCRIPTION OF THE DRAWING

The objects, advantages and features of this invention will be more clearly perceived from the following detailed description, when read in conjunction with the accompanying drawing, is which.

DETAILED DESCRIPTION OF THE PREFERRED EMBODIMENTS

Figure 1:
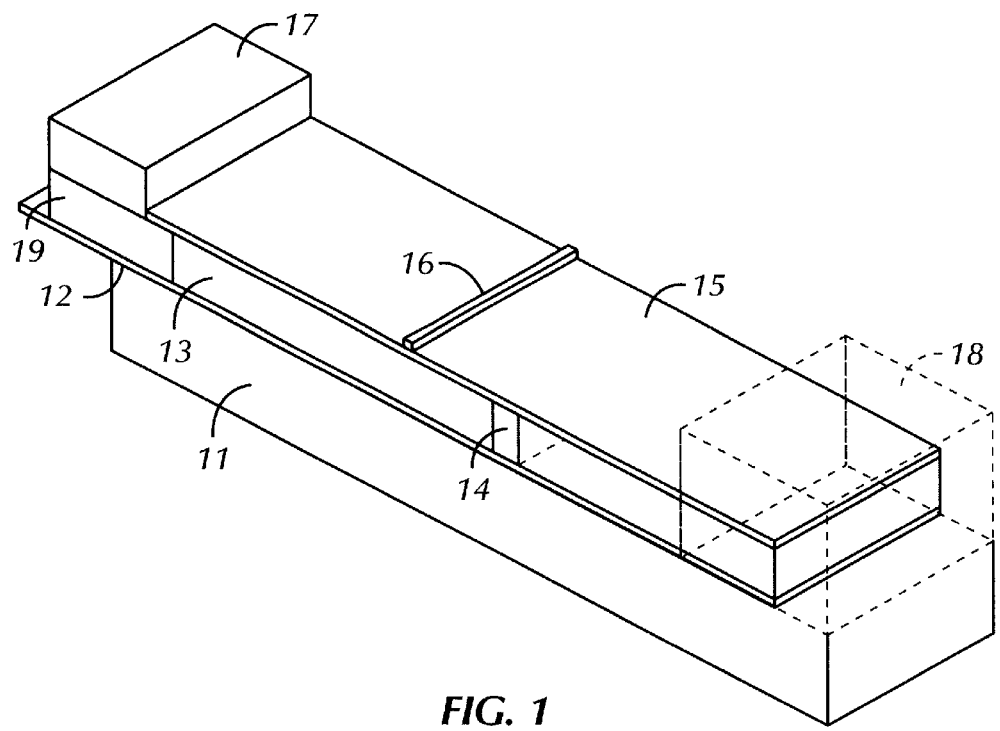
FIG. 1 is a schematic perspective, partially phantom, view of an embodiment of the invention.
Figure 2:
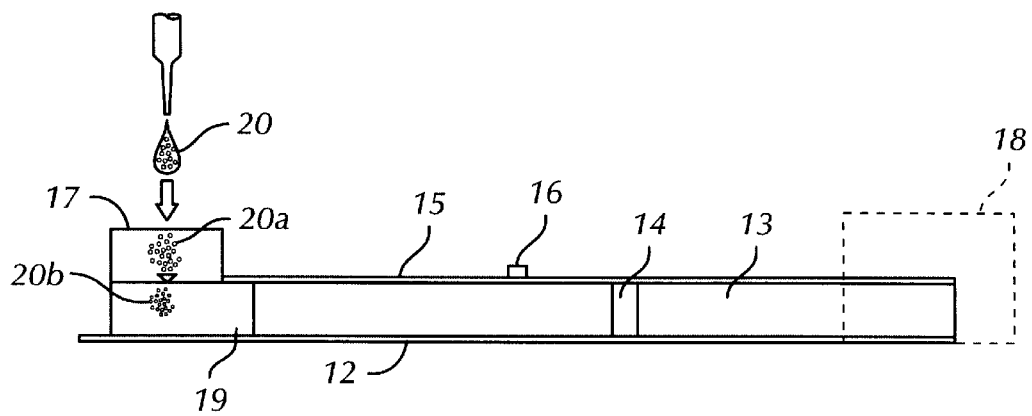
FIG. 2 is a schematic side view of the FIG. 1 embodiment.

With reference now to the drawing, and more particularly to FIGS. 1 and 2, there is shown an embodiment of the present invention, a lateral flow test strip for an immunochromatographic assay. A relatively rigid assay support member 11 serves as a base and provides support for the test strip, which in this embodiment is removable from the support. On top of the support member is backing member 12 on which is mounted porous membrane 13. The backing member is removably adhered to the support, or it may itself be an adhesive layer. Within the porous membrane is capture zone 14. The capture zone is formed by striping with antigens or antibodies, for example, as is well known in the art. On top of the porous membrane is non-light transmissive cover or surface 15. The cover or surface may be considered to be optically opaque, at least to the extent that capture zone indicia would not be visible through cover 15. The protective membrane may be made of plastic, glass or paper, for example, or any practical combination thereof. A printed standard or calibration line 16 is situated on top of the cover and provides information utilized by the assay reader after the test has been accomplished. This is contemplated to be a magnetic stripe with the information the reader needs.

At the left end, as shown in FIGS. 1 and 2, is sample pad 17, through which an analyte-containing sample solution 20 is administered to the porous membrane, with analytes 20a shown in the sample pad. The sample pad may also include conjugate pad 19 which is in communication with the porous membrane. Within the conjugate pad are superparamagnetic beads or particles which are coupled with antibodies, the combination of a bead and an antibody being referred to as a conjugate, a plurality of them being labeled with reference numeral 20b. These conjugates are configured to combine with target analytes in the sample solution in a known manner to create a sandwich assay, well known in the art, where the beads provide labels for the target analytes. Competitive assay techniques, also well known in the art, could also be employed.

The porous membrane will, as a feature of some embodiments, have a wicking pad 18 at the opposite, or right, end of the test strip. This is a conventional element.

The operation of the lateral flow assay is well known. The labeled analytes (in a sandwich assay, for example) move by capillary action from the left to the right as seen in FIG. 1. Labeled analytes are captured in the capture zone where reading of the assay results is accomplished. Wicking pad 18 enhances capillary flow in the porous membrane by "pulling," or "driving" the fluid through the porous membrane. A typical material from which the porous membrane is made is nitrocellulose.

While the capillary action and the existence of a capture zone are well known and conventional, the manner in which the described embodiments of the invention detect the presence and the quantity of the target analytes differs greatly from the prior art. The known lateral flow assays depend upon color or fluorescence to provide a visual or optical indication of the presence of target analytes in the capture zone, but the ability of optical techniques to detect the presence of the target analytes is limited. A relatively low concentration of target analytes in the sample can result in so few captured analytes as to be optically undetectable on the surface of the porous membrane at the capture zone. Further, the optical intensity of the capture zone with the captured analytes is only a rough function of the quantity of target analytes captured. However, there is no way to accurately measure the total quantity of captured analytes within the capture zone because only the surface is optically readable.

The present embodiment provides greatly enhanced sensitivity and quantitative accuracy because the magnetic labeled analytes in the capture zone are detectable by a suitable magnetic detector to the extent of the target analytes within the entire volume of the capture zone.

Figure 3:
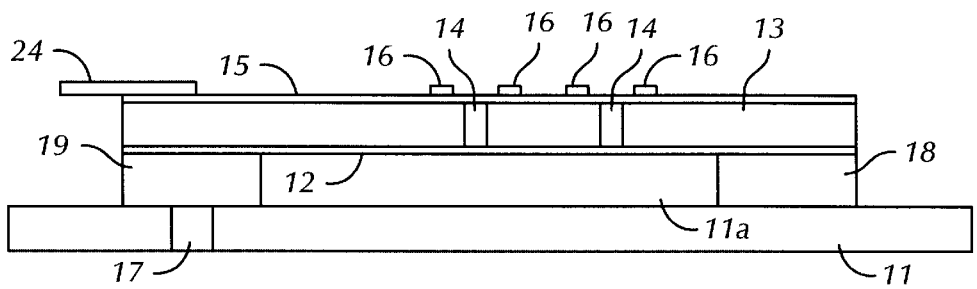
FIG. 3 is a schematic side view of a preferred embodiment of the invention.
Figure 4:
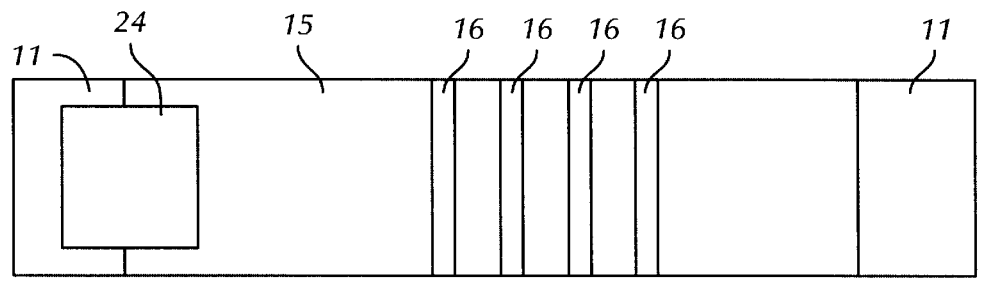
FIG. 4 is a top view of the FIG. 3 embodiment.
Figure 5:
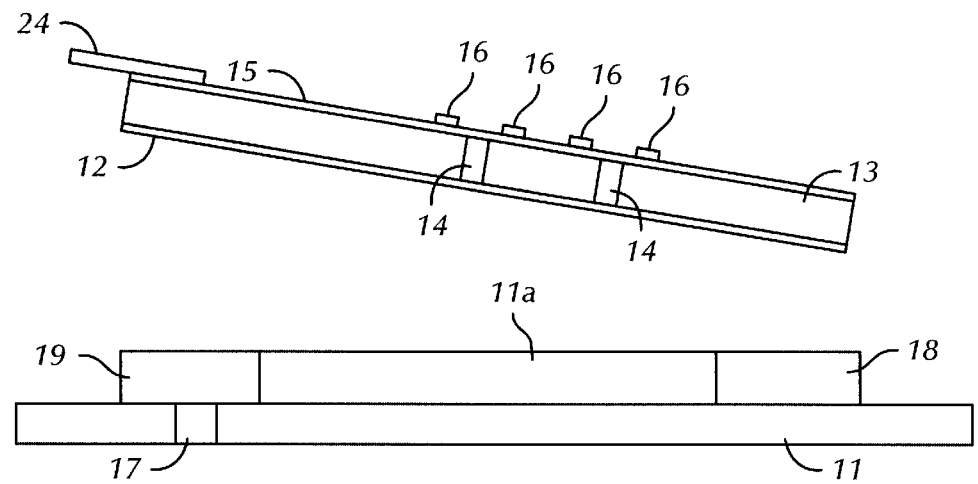
FIG. 5 shows how the test strip of FIG. 3 is removed.

Additional features may be added, including additional capture zones 14 (two are shown in FIGS. 3 and 5) and additional calibration lines 16. In FIGS. 3–5 there are four calibration lines, one before and one after each capture zone. There could be several capture zones and equivalent calibration lines.

Figure 6:
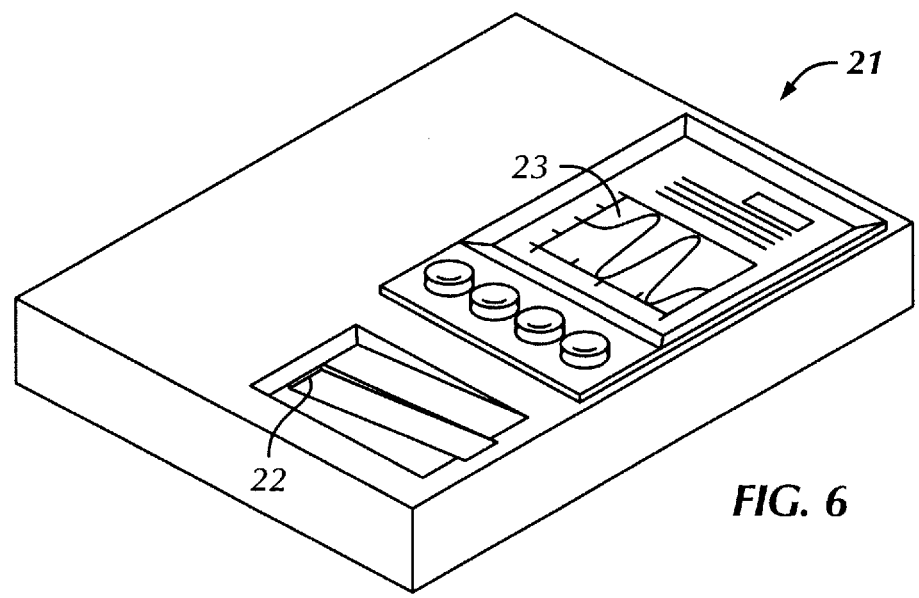
FIG. 6 is a perspective of a reader device used with the assay apparatus of FIG. 1 or 3.
Figure 7:
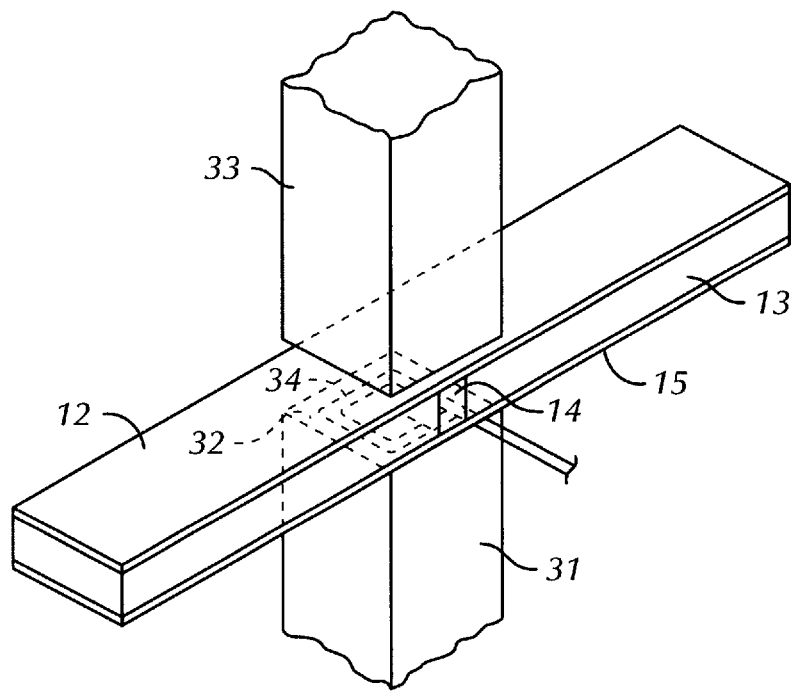
FIG. 7 schematically shows how the assay strip is read by a magnetic reader device.

A significant aspect of an embodiment of the invention is the means and manner of magnetically reading the assay. A magnetic reader 21 of the type contemplated is shown in FIG. 6. This employs the technology disclosed in PCT publication WO 99/27369, to determine the presence of target analytes and their quantity. The reader of the present invention is contemplated to be portable, that is, approximately pocket size, so that it is easily employed in the field. It will provide accurate assay readings even under stressful conditions and in poor light. The apparatus of FIG. 6 has a narrow slit opening 22 into which an assay strip can be inserted for reading by electromagnetic means. The analyte quantity may be shown in window 23, which could be an LED or an LCD screen, for example. The manner in which the capture zone with analytes bonded therein is read is shown schematically in FIG 7. Lower electromagnetic head 31 has a top surface 32 on which is mounted detection coil 34 and across which strip 13/15 is positioned with capture zone 14 centered over the detection coil. The strip is shown in this example with surface or cover 15 of the strip actually touching the surface of the detection coil. Cover 15 thus protects the delicate structure of the porous membrane during the reading process, as well as long term if the strip is archived. Top magnet 33 is closely adjacent to the opposite side of the strip which has stripping layer 12 thereon. The structure of the electromagnetic head shown in FIG. 7 is generally equivalent to that in reader 21.

To enable the reader of FIG. 6 to be employed to read the analytes in the capture zone, the test strip is made readily removable from support member 11, and from sample pad 17 and wicking pad 18. As seen in FIGS. 3–5, pull tab 24 is secured to cover 15, which is, in turn, secured to porous membrane 13. The porous membrane is removably secured to the support by means of a removable backing 12 which is secured to the bottom of the porous membrane. It will be noted that the assay is essentially inverted as shown here. The sample could be applied to sample pad 17 with the strip turned over from the position of FIGS. 3 and 5. In this reverse position conjugate pad 19 and the wicking pad 18 are positioned between support member 11 and the peelable strip 12, 13, 15. Element 11a may be a non-active polymer fill membrane. Sheet or adhesive 12 is readily removable from the surfaces of elements 18, 19 and 11a.

It is contemplated that the test strip, primarily consisting of the porous membrane and protective surfaces thereof, may be made sufficiently rigid to not need a support member. Such a configuration would not need to be stripped from anything. The reader apparatus might have to be modified somewhat to handle the different configuration of the test strip, but the principle of magnetic reading shown in FIG. 7 still applies.

FIG. 5 shows how the test strip, comprised of the cover, porous membrane and removable backing, is removed from the support member. In actuality, this removed test strip is typically about 3–12 mm wide, and only about 150–500$\mu$ thick. This strip is easily fed into reader 21 for a digital readout, which readout may be shown on the screen or printed on paper in any desired form by reader 21. The exposed test strip is stable and can be archived either before or after being read. Since the superparamagnetic beads are magnetized only during the reading process, the exposed test strip is not subject to degradation. The analytes contained in the capture zone remain there, labeled with the conjugate combination.

Alternative features of the embodiment discussed above contemplate the test strip being slid off the support member or peeled off, either manner of removal being physically possible.

The opaque surface or cover 15 has several positive functions. Contrary to prior art optical lateral flow assays, where very faint lines can easily be misinterpreted in the field, especially in stressful situations or low light conditions, there is no possibility of misinterpretation of test results with this invention. Optically read assays, especially those visually read, are also subject to operator bias. In the present invention the reader reads the total number of labeled analytes in the capture zone without inherent sources of error as mentioned above. Further, the thickness of the opaque cover precisely positions the porous membrane and thus, the capture zone, with respect to the magnet head and detection coil 34. Since the test strip actually touches the detection coil, without the protective surface the porous nitrocellulose membrane would be damaged by rubbing across detection coil 34, thereby possibly producing incorrect or unreliable readings, or both. Although being very thin, in the range of 30–50$\mu$ the cover protects against physical damage and environmental contamination as well as providing precise positioning for accurate electromagnetic readings.

While the present invention has been illustrated and described by means of a specific embodiment, it is to be understood that numerous changes and modifications can be made therein without departing from the scope of the claims and equivalents thereto.

What is claimed is:

1. A lateral flow assay device for quantitative detection of target analytes in a sample, said device comprising:
   an assay support member having a first end and a second end;
   a sample receiving element at one end of said support member for introduction of the sample to be analyzed into said device; and
   an immunoassay test strip comprising:
      a porous analytical membrane removably mounted adjacent to and generally parallel with said support member, said analytical membrane having a first end and a second end;
      at least one capture region in said analytical membrane intermediate said first and second ends thereof, said at least one capture region being configured to capture a labeled analyte moving from said first end of said analytical membrane toward said second end of said analytical membrane;
      a backing member between said analytical membrane and said support member to facilitate removal of said analytical membrane from said support member for reading the assay and for archiving said test stripy;
      a protective membrane covering said analytical membrane on the side opposite to said support member, said protective membrane being optically non-transparent; and
      at least one magnetic standard line printed on said protective membrane.

2. The device recited in claim 1, wherein said protective membrane is formed integrally with said porous membrane.

3. The device recited in claim 1, wherein said protective membrane is formed pursuant to a surface treatment of said porous membrane.

4. The device recited in claim 1, and further comprising a control region in said porous membrane for collection of magnetic conjugates that have passed through the capture region to indicate that said test strip has been used.

5. The device recited in claim 1, wherein said protective membrane is formed of material selected from the group consisting of plastic, glass and paper.

6. The device recited in claim 1, and further comprising superparamagnetic particles in said sample receiving element, said particles being configured to bind with target analytes in the sample.

* * * * *